United States Patent [19]

Schnegg et al.

[11] 4,401,833

[45] Aug. 30, 1983

[54] PROCESS FOR THE PREPARATION OF 4-CHLORO-2,6-DIALKYLANILINES

[75] Inventors: Ulrich Schnegg, Leverkusen; Karlfried Wedemeyer, Cologne, both of Fed. Rep. of Germany

[73] Assignee: Bayer Aktiengesellschaft, Leverkusen, Fed. Rep. of Germany

[21] Appl. No.: 315,767

[22] Filed: Oct. 28, 1981

[30] Foreign Application Priority Data

Nov. 15, 1980 [DE] Fed. Rep. of Germany ....... 3043206

[51] Int. Cl.³ ............................................. C07C 85/00
[52] U.S. Cl. .................................................. 564/412
[58] Field of Search ........................................ 564/412

[56] References Cited

U.S. PATENT DOCUMENTS

| | | | |
|---|---|---|---|
| 1,730,729 | 10/1929 | Hoffa et al. | 564/412 |
| 2,675,409 | 4/1954 | Orloff et al. | 564/412 |
| 3,396,195 | 8/1968 | Visser | 564/412 |
| 3,396,200 | 8/1968 | George et al. | 564/412 X |

FOREIGN PATENT DOCUMENTS

| | | |
|---|---|---|
| 2337621 | 2/1974 | Fed. Rep. of Germany . |
| 2288083 | 5/1976 | France . |
| 50-46633 | 4/1975 | Japan .................................. 564/412 |

OTHER PUBLICATIONS

Acta Chemica Scandinavica 19 (1965), vol. 19, No. 9, Copenhagen H. Hjeds et al, "Oximes, O-Methyl-oximes and N-Methyloximes of 2.6-Dimethyl-4-halogenobenzaldehyde", pp. 2166–2174.

*Primary Examiner*—Paul F. Shaver
*Attorney, Agent, or Firm*—Sprung, Horn, Kramer & Woods

[57] ABSTRACT

Process for the preparation of 4-chloro-2,6-dialkylanilines, characterized in that the ammonium salts of the 2,6-dialkylanilines are reacted with a chlorination agent at $-15°$ to $100°$ C. in the presence of an inert organic solvent and/or diluent and, if necessary, the presence of Friedel-Crafts catalysts, and 4-chloro-2,6-dialkylaniline is then liberated from the 4-chloro-2,6-dialkylanilinium salt obtained.

20 Claims, No Drawings

PROCESS FOR THE PREPARATION OF 4-CHLORO-2,6-DIALKYLANILINES

The invention relates to a process for the preparation of 4-chloro-2,6-dialkylanilines by chlorination of the corresponding 2,6-dialkylanilines.

A process for the preparation of 2,4,6-trichloroanilines, in which the corresponding aniline hydrochlorides, in an inert organic solvent system, are reacted with excess chlorine, is known from U.S. Pat. No. 2,675,409.

A similar process is described in (German Offenlegungsschrift) No. 2,319,645. According to this published specification 5-chloro-2-toluidine is prepared by reaction of o-toluidine hydrochloride, suspended in halogenohydrocarbons, with chlorine.

It is mentioned in German Offenlegungsschrift No. 2,916,714 on page 5, penultimate paragraph, that 4-chloro-2,6-dialkylanilines can be prepared by chlorination of the corresponding aniline compounds. More precise details on the chlorination process and the yields of chlorination products thereby obtained are, however, not to be found therein.

The preparation of 4-chloro-2,6-dimethylaniline by direct chlorination of 2,6-dimethylaniline in glacial acetic acid is described in J.Chem.Soc. 1927, pages 1106, 1107. In this process, however, only poor yields of chlorination product are obtained, for which reason the authors point out that the direct chlorination of 2,6-dimethylaniline is not very suitable for the preparation of 4-chloro-2,6-dimethylaniline.

Apart from the disadvantage of poor yields the process described in J.Chem.Soc. 1927, pages 1106, 1107 has even further disadvantages. Because the chlorination is carried out in glacial acetic acid, it is necessary, in order to isolate the chlorination product, to dilute the glacial acetic acid with water and to neutralize the solution containing acetic acid with alkali. The salt of acetic acid thus formed, for example sodium acetate, which can only be separated with difficulty, therefore goes into the waste liquor, where is not only greatly increases the salt load, but also the chemical and biological oxygen demand.

A process for the preparation of 4-chloro-2,6-dialkylanilines has now been found, which is characterized in that the ammonium salts of the 2,6-dialkylanilines are reacted with a chlorination agent at $-15°$ to $100°$ C. in the presence of an inert organic solvent and/or diluent and, if desired, in the presence of a Friedel-Craft catalyst and 4-chloro-2,6-dialkylaniline is then liberated from the 4-chloro-2,6-dialkylanilinium salt obtained.

2,6-Dialkylanilines which can be employed in the process according to the invention are those of the formula

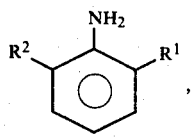

wherein $R^1$ and $R^2$ are identical or different and represent an alkyl radical with 1 to 4, preferably 1 or 2, carbon atoms.

For example the following 2,6-dialkylanilines can be employed in the process according to the invention: 2,6-dimethylaniline, 2-ethyl-6-methylaniline, 2-isopropyl-6-methylaniline, 2,6-diethylaniline, 2-ethyl-6-n-propylaniline, 2-n-propyl-6-methylaniline and 2-ethyl-6-isopropylaniline.

2,6-Dimethylaniline 2,6-diethylaniline and 2-ethyl-6-methylaniline are preferably employed.

The process according to the invention is carried out, in general, as follows: 2,6-dialkylaniline is dissolved or suspended in an inert organic solvent and/or diluent and the 2,6-dialkylanilinium salt is then precipitated with proton acids, such as hydrochloric acid, sulphuric acid or phosphoric acid, preferably hydrochloric acid.

One can, of course, also add aqueous acid to the 2,6-dialkylaniline in an inert organic solvent and/or diluent and then to distil off the water, for example by azeotropic distillation. A further method for preparing the ammonium salts of the 2,6-dialkylanilines consists, for example, in preparing the salt by means of a proton acid in any desired solvent and/or diluent, for example in water, independently of the solvent and/or diluent used for the chlorination process, separating off the 2,6-dialkylanilinium salt obtained and using it as such in the process according to the invention.

Inert organic solvents and/or diluents which are usually employed in the process according to the invention are those in which the solubility of the 2,6-dialkylanilinium salt is low, so that the bulk of the salt is present in crystalline form as a suspension. Because the selectivity and the yields in the chlorination process are larger, the smaller the solubility of the anilinium salt in the solvent and/or diluent employed, whilst on the other hand the rate of reaction increases with the solubility of the anilinium salt, it is expedient to find a technically sensible compromise between highest selectivity and greatest space/time yield. In order to achieve an optimum in selectivity and space/time yield a solubilizing agent, which is often a polar organic solvent, can be added to a non-polar organic solvent with poor solvent properties. Because the optimum solubility of the anilinium salt in the inert organic solvent and/or diluent employed depends on various factors, such as the two alkyl radicals of the dialkylaniline and the type of proton acid as well as its solubility in the solvent and/or diluent, it is expedient, before the actual reaction, to determine the most suitable solvent and/or diluent for the chlorination by means of preliminary experiments which are easy to carry out.

Aromatic and aliphatic hydrocarbons or aliphatic halogenohydrocarbons with 1 to 15, preferably 1 to 8, carbon atoms, such as methylene chloride, carbon tetrachloride, trichloroethane, hexane, isooctane, benzene, toluene or xylene, preferably carbon tetrachloride, isooctane or toluene, can be employed in the process according to the invention as inert organic solvents and-/or diluents. Furthermore, the inert organic solvents and/or diluents can also contain proton acids, such as hydrochloric acid, sulphuric acid or phosphoric acid, dissolved in quantities up to saturation.

Lower alcohols, such as methanol, ethanol or propanol, lower carboxylic acids and carboxylic acid derivatives, such as acetic acid or dimethylformamide, and/or cyclic ethers, such as tetrahydrofuran or dioxane, can be employed in the process according to the invention to increase the solubility of the anilinium salts in the solvents and/or diluents employed.

The quantity of solvents and/or diluents to be employed, either individually or mixed together, can vary within wide ranges. In general, about 500 to 3,000 ml, preferably 750 to 1,500 ml, relative to 1 mol of dialkylaniline, are employed.

Chlorination agents customarily used are chlorine gas or gas mixtures containing chlorine gas, such as a mixture of chlorine and air, chlorine and carbon dioxide, chlorine and hydrogen chloride or chlorine and nitrogen. However, it is also possible to use other chlorination agents, such as sulphuryl chloride, in the process according to the invention.

In general, 0.8 to 1.8, preferably 1.0 to 1.5, mols of chlorine are used per mol of starting material, when chlorine gas or mixtures containing chlorine gas are employed.

If another chlorination agent, such as sulphuryl chloride, is employed, the amount of chlorination agent to be used is about 0.8 to 1.5, preferably 0.9 to 1.2, mols of chlorination agent per mol of starting material.

The chlorination reaction can be advantageously carried out in the presence of customary Friedel-Crafts catalysts, such as $FeCl_3$, $AlCl_3$ and/or iodine.

The quantity of Friedel-Crafts catalysts is not critical in this reaction. In general, about 0.1 to 10 mol %, preferably 0.5 to 5 mol %, relative to dialkylaniline, are used.

The process according to the invention is usually carried out at about $-15°$ to $100°$ C., preferably at $0°$ to $80°$ C.

The process can be carried out continuously as well as discontinuously at normal pressure and also at increased pressure (approximately 1.0 to 1.5 bar).

The by-products formed during the chlorination of the 2,6-dialkylanilines can be removed from the reaction mixture, in a manner which is in itself known, after termination of the chlorination reaction. Thus, when carbon tetrachloride is used as solvent and/or diluent, the reaction mixture can be subjected to hydrolysis with water or aqueous acid. The anilinium salts can then be separated in a suitable manner, for example by distillation, from the suspension, if necessary after removal of water, and the anilines can be liberated with alkali in an aqueous medium. After separation from the solution of the salt the crude 4-chloro-2,6-dialkylaniline can be further purified by distillation. In this manner of working up, the hydrolyzable by-products remain in the carbon tetrachloride phase.

According to another variant it is also possible to extract the chlorination mixture with dilute acid, the anilinium salts going over into the aqueous phase, from which the crude 4-chloro-2,6-dialkylaniline is liberated with alkali.

Furthermore, it is possible to add water or an aqueous acid to the reaction mixture and then to distill the solvent and/or diluent and the crude 4-chloro-2,6-dialkylaniline with steam.

In the process according to the invention, the hydrolysis of the crude mixture is in the interests of operational safety, since hydrolysable by-products formed easily decompose under the thermal conditions of a distillation.

The 4-chloro-2,6-dialkylanilines are obtained in good yields and in high purity in the process according to the invention. In this connection it is extraordinarily surprising that the isomers 3-chloro-2,6-dialkylaniline and 5-chloro-2,6-dialkylaniline cannot be detected in the crude product, so that the working up and purification of the crude product can be carried out simply and therefore economically.

It was in fact to be expected that the isomers 3-chloro-2,6-dialkylaniline and 5-chloro-2,6-dialkylaniline as well as 3,4-dichloro-2,6-dialkylaniline and 4,5-dichloro-2,6-dialkylaniline would be formed in considerable amounts, besides the desired 4-chloro-2,6-dialkylaniline, in the chlorination of the anilinium salts.

The selective chlorination of the 2,6-dialkylanilines to form 4-chloro-2,6-dialkylanilines in the process according to the invention is also to be seen as particularly surprising with respect to German Offenlegungsschrift No. 2,319,645, according to which o-toluidine hydrochloride is reacted with chlorine in the presence of halogenohydrocarbons as solvent to form 5-chloro-2-toluidine. According to this, it was in fact to be expected that the chlorination of 2,6-dialkylaniline in the form of its hydrochloride would give the same isomer as the chlorination of the corresponding acetamide. However, the chlorination of 2,6-dialkylacetanilide gives 3-chloro-2,6-dialkylacetanilide, as our own investigations have shown. The absence of the 3,4-dichloro-2,6-dialkylaniline and 4,5-dichloro-2,6-dialkylaniline to be expected according to the German Offenlegungsschrift given above must also be seen as particularly surprising.

The 4-chloro-2,6-dialkylanilines prepared according to the invention are used as intermediate products for plant protection agents (German Offenlegungsschrift No. 2,916,714).

The process according to the invention is to be illustrated by the following examples, without, however, being limited to these examples.

EXAMPLE 1

3 Mols of 2,6-dimethylaniline are dissolved in 2,300 g of $CCl_4$ and 30 g of ethanol in a 3 l faceground beaker. HCl gas is then introduced at room temperature until saturation is reached. After saturation is complete, the mixture is cooled to $10°$ to $15°$ C. and, at this temperature, 270 g of chlorine are passed through the suspension formed, in the course of 4 hours. After termination of the chlorination process 250 ml of 15% strength hydrochloric acid are added to the solution and the hydrochloric acid is then distilled off again azeotropically. After cooling to $20°$ C., the crude 4-chloro-2,6-dimethylaniline hydrochloride, in the form of colourless crystals, is filtered off with suction. If the salt is taken up in water and the solution neutralised with sodium hydroxide solution, 331 g of an aniline mixture, which consists of 14% of 2,6-dimethylaniline and 84% of 4-chloro-2,6-dimethylaniline, is obtained. The yield, relative to the amount of 2,6-dimethylaniline reacted, is 69%.

The pure product, which has a purity of 99%, determined by gas chromatography, and a melting point of $42°$ C., is obtained by fractional distillation of the crude product at $115°$ to $117°$ C./5 mm Hg.

EXAMPLE 2

Example 1 is repeated, but with toluene as solvent instead of the mixture of $CCl_4$/ethanol. After extraction of the crude aniline hydrochloride with dilute hydrochloric acid and liberation of the base with NaOH, 357 g of a crude 4-chloro-2,6-dimethylaniline are obtained, which contains, besides 54% of 2,6-dimethylaniline, 46% of 4-chloro-2,6-dimethylaniline. The yield, relative to the amount of 2,6-dimethylaniline reacted, is 75%.

EXAMPLE 3

3 Mols of 2-ethyl-6-methylaniline in CCl$_4$ are treated first with hydrogen chloride and then with chlorine gas, analogously to Example 1. After the usual working up process the crude 4-chloro-2-ethyl-6-methylaniline hydrochloride is obtained in the form of colourless crystals, from which 334 g of crude amine mixture are liberated. A gas-chromatogram of the crude amine indicates 12% of 2-ethyl-6-methylaniline besides 88% of 4-chloro-2-ethyl-6-methylaniline, corresponding to a yield of 66% relative to reacted starting material.

4-Chloro-2-ethyl-6-methylaniline, pure according to gas chromatography, is obtained from the crude mixture of products at a head temperature of 139° C./13 mm Hg.

EXAMPLE 4

Example 3 is repeated, but instead of carbon tetrachloride, toluene is used as solvent and the chlorine is introduced at 80° C. After the usual working up process, 363 g of aniline mixture are obtained, which contains 22% of starting material in addition to 73% of 4-chloro-2-ethyl-6-methylaniline. The yield, relative to reacted aniline, is 64%.

EXAMPLE 5

Example 3 is repeated with 2,6-diethylaniline, the chlorine being introduced, however, in the presence of 10 g of iodine as a catalyst. After the usual working up process 279 g of an amine mixture are obtained, which contains, according to gas chromatography, 39% of diethylaniline in addition to 45% of 4-chloro-2,6-diethylaniline. This corresponds to a yield of 60%, relative to reacted diethylaniline.

The distillation at 102° C./0.2 mm Hg yields the product, which is pure according to gas chromatography.

EXAMPLE 6

Example 1 is repeated, but with the ethanol omitted and the chlorine replaced by sulphuryl chloride, which is added at a temperature of 45°–50° C., as the chlorination agent. 4-Chloro-2,6-dimethylaniline is obtained in 70% yield by a steam distillation of the crude product which has been treated with alkali.

What is claimed is:

1. A process for the preparation of a 4-chloro-2,-6-dialkylaniline which comprises contacting the ammonium salt of a 2,6-dialkylaniline with a chlorination agent at −15° to +100° C. in the presence of an inert organic solvent and/or diluent and, thereafter, liberating 4-chloro-2,6-dialkylaniline from the corresponding 4-chloro-2,6-dialkylanilinium salt so-obtained.

2. A process according to claim 1, wherein the process is carried out in the presence of a Friedel-Crafts catalyst.

3. A process according to claim 1, wherein the chlorination mixture is subjected to hydrolysis with water or aqueous acid.

4. A process according to claim 1, wherein the chlorination agent is chlorine gas, sulphuryl chloride or a gas mixture containing chlorine and/or sulphuryl chloride.

5. A process according to claim 1, wherein the chlorination agent is employed in an amount of 0.8 to 1.5 mols per mol of ammonium salt of 2,6-dialkylaniline.

6. A process according to claim 1, wherein the inert organic solvent and/or diluent is an aromatic and/or aliphatic hydrocarbon and/or aliphatic halogenohydrocarbon with 1 to 15 carbon atoms.

7. A process according to claim 1, wherein the inert organic solvent and/or diluent is carbon tetrachloride, isooctane, toluene or a mixture thereof.

8. A process according to claim 1, wherein the inert organic solvent and/or diluent is present in an amount of 500 to 3,000 ml per mol of ammonium salt of 2,6-dialkylaniline.

9. A process according to claim 2, wherein the Friedel-Crafts catalyst is FeCl$_3$, AlCl$_3$ and/or iodine.

10. A process according to claim 2, wherein the Friedel-Crafts catalyst is employed in an amount of from 0.1 to 10 mol %, based upon the weight of starting material.

11. A process according to 1, wherein the process is carried out at a temperature of 0° to 80° C.

12. A process according to claim 1, wherein the 2,6-dialkylaniline is one having the formula

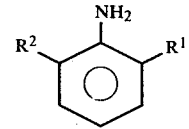

wherein R$^1$ and R$^2$ are independently alkyl radicals with 1 to 4 carbon atoms.

13. A process according to claim 12, wherein at least one of R$_1$ and R$_2$ is methyl.

14. A process according to claim 12, wherein at least one of R$_1$ and R$_2$ is ethyl.

15. A process according to claim 12, wherein both R$_1$ and R$_2$ are methyl.

16. A process according to claim 12, wherein both R$_1$ and R$_2$ are ethyl.

17. A process according to claim 12, wherein R$_1$ is methyl and R$_2$ is ethyl.

18. A process according to claim 1, wherein said inert solvent is carbon tetrachloride.

19. A process according to claim 18, wherein said carbon tetrachloride is an admixture with ethanol.

20. A process according to claim 1, wherein said inert organic solvent is toluene.

* * * * *